(12) United States Patent
Lowe et al.

(10) Patent No.: US 7,923,678 B2
(45) Date of Patent: Apr. 12, 2011

(54) SENSING METHOD INCLUDING INTERROGATION OF A HOLOGRAPHIC SENSOR

(75) Inventors: Christopher Robin Lowe, Cambridge (GB); Jeffrey Blyth, Cambridge (GB); Anthony Peter James, Warickshire (GB)

(73) Assignee: Cambridge Enterprise Limited, Cambridge (GB)

( * ) Notice: Subject to any disclaimer, the term of this patent is extended or adjusted under 35 U.S.C. 154(b) by 25 days.

(21) Appl. No.: 11/572,223

(22) PCT Filed: Jul. 19, 2005

(86) PCT No.: PCT/GB2005/002861
§ 371 (c)(1),
(2), (4) Date: Jun. 5, 2007

(87) PCT Pub. No.: WO2006/008531
PCT Pub. Date: Jan. 26, 2006

(65) Prior Publication Data
US 2008/0094635 A1  Apr. 24, 2008

(30) Foreign Application Priority Data
Jul. 19, 2004  (GB) .................................. 0416140.2

(51) Int. Cl.
*G01J 1/04*   (2006.01)
*G01B 11/16*  (2006.01)
*G03H 1/00*   (2006.01)

(52) U.S. Cl. .......................... 250/227.14; 356/32; 359/2

(58) Field of Classification Search .................. 250/221, 250/214 R, 216, 237 G, 231.1, 227.14; 356/32, 356/35.5; 359/2, 3, 5
See application file for complete search history.

(56) References Cited

U.S. PATENT DOCUMENTS

| | | | |
|---|---|---|---|
| 4,631,222 A * | 12/1986 | Sander | 428/841 |
| H371 H * | 11/1987 | Bobb | 324/244.1 |
| 5,682,236 A | 10/1997 | Trolinger et al. | |
| 5,857,709 A | 1/1999 | Chock | |
| 5,989,923 A * | 11/1999 | Lowe et al. | 436/518 |
| 6,482,489 B1 * | 11/2002 | Otaki et al. | 428/40.1 |
| 2002/0186928 A1 | 12/2002 | Curtis | |
| 2005/0251339 A1 * | 11/2005 | Araki et al. | 702/2 |

FOREIGN PATENT DOCUMENTS

| | | |
|---|---|---|
| EP | 0 345 405 A2 | 12/1989 |
| GB | 2 232 927 A | 1/1991 |
| JP | A S62-102139 | 5/1987 |
| JP | 04-351948 | 12/1992 |
| JP | A H8-503542 | 4/1996 |
| JP | A 2001-200495 | 7/2001 |
| WO | WO 94/10538 | 5/1994 |
| WO | WO 9963408 A1 * | 12/1999 |

(Continued)

OTHER PUBLICATIONS

Chen, G. et al., "A New Temperature- and pH-responsive Copolymer for Possible Use in Protein Conjugation," *Macromolecular Chemistry and Physics*, 1995, vol. 196, pp. 1251-1259.

(Continued)

*Primary Examiner* — Thanh X Luu
(74) *Attorney, Agent, or Firm* — Saliwanchik, Lloyd & Eisenschenk

(57) ABSTRACT

A sensing method, which comprises subjecting a holographic sensor to an external physical interaction to which the sensor is sensitive, and observing a change in the holographic image.

17 Claims, 3 Drawing Sheets

FOREIGN PATENT DOCUMENTS

WO    WO 03/087899    4/2003

OTHER PUBLICATIONS

Marshall, A. J. et al., "pH-sensitive Holographic Sensors," *Analytical Chemistry*, Sep. 1, 2003, vol. 75, No. 17, pp. 4423-4431.

Xue, S. S. et al., "Holographic and spectroscopic characterization of spiropyran doped poly(methyl metacrylate) films," *Thin Solid Films*, Dec. 15, 1994, vol. 253, No. 1-2, pp. 228-232.

Zaidi, N. A. et al,, "Room temperature magnetic order in an organic magnet derived from polyaniline," *Polymer*, Jul. 21, 2004, vol. 45, No. 16, pp. 5683-5689.

Japanese Office Action dated Feb. 9, 2010 in corresponding Japanese Application No. 2007-522023.

* cited by examiner

SENSING METHOD INCLUDING INTERROGATION OF A HOLOGRAPHIC SENSOR

CROSS-REFERENCE TO A RELATED APPLICATION

This application is a National Stage Application of International Application Number PCT/GB2005/002861, filed Jul. 19, 2005; which claims priority to Great Britain Application No. 0416140.2, filed Jul. 19, 2004.

FIELD OF THE INVENTION

This invention relates to a method for changing an optical characteristic of a holographic sensor.

BACKGROUND TO THE INVENTION

Holographic sensors may be used for the detection of a variety of analytes. WO95/26499 discloses a holographic sensor, based on a volume hologram. This sensor comprises an analyte-sensitive matrix having an optical transducing structure disposed throughout its volume. Because of this physical arrangement of the transducer, an optical signal generated by the sensor is very sensitive to volume changes or structural rearrangements taking place in the analyte-sensitive matrix as a result of interaction or reaction with the analyte.

WO03/087899 describes a method of continuous sensing using a holographic sensor. A fluid comprising the analyte is passed over the sensor, the analyte reacting reversibly with the holographic support medium.

SUMMARY OF THE INVENTION

The present invention is based on the realization that a holographic sensor can usefully be sensitive to physical interaction, e.g. in the presence of a change of temperature, magnetic, electric or other radiation field, light and/or pressure. The sensor, e.g. a volume hologram in which a medium supporting a hologram is affected by the physical interaction, undergoes a change that can be observed. This change in an optical characteristic is preferably reversible.

According to the invention, a sensing method comprises subjecting a holographic sensor to an external physical influence to which the sensor is sensitive, and observing a change in the image. The physical influence may be understood as remote or direct interrogation that induces a variation in a physical property of a medium in which a holographic element is supported.

The holographic sensor may be sensitive to a physical influence such as temperature, magnetism, light and/or pressure. The invention has particular relevance to security/authentication. The observed change, i.e. a change in the optical characteristic of the sensor, may be detectable either directly by eye, or using any suitable apparatus, for example a spectrometer.

DESCRIPTION OF THE INVENTION

Figure 3:
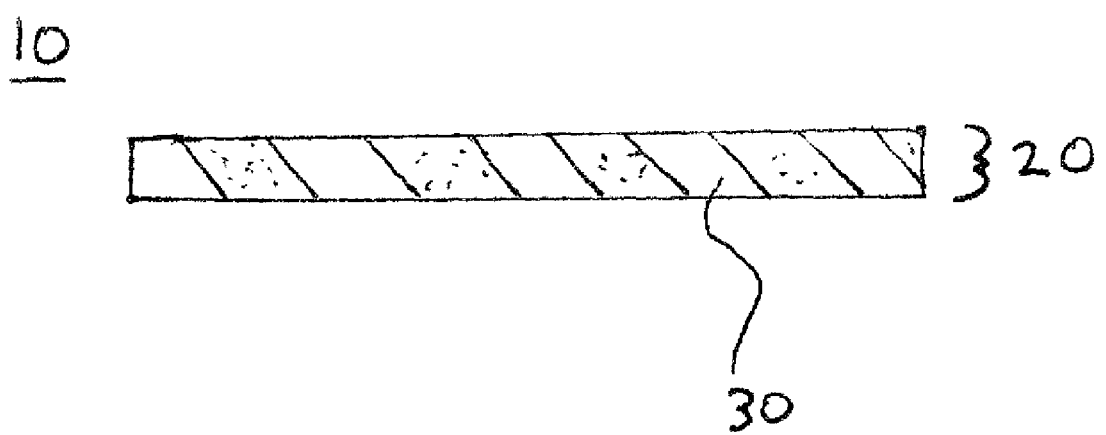
FIG. 3 is a side view of a holographic sensor comprising a volume hologram recorded in a support medium, according to an embodiment.

A holographic sensor for use in the invention typically comprises a holographic support medium and, disposed throughout the volume of the medium, a hologram. FIG. 3 is a side view of a holographic sensor 10 comprising a volume hologram 20 recorded in a support medium 30. according to an embodiment. A method of the invention preferably involves the use of a sensor wherein the support medium is sensitive to a physical property, e.g. temperature. By subjecting the sensor to interrogation, the (local) physical property may be changed, causing a change in a property of the support medium. This results in a change in an optical characteristic of the element.

The sensor may be interrogated by any suitable means. As an example of remote interrogation, a laser of suitable power, when directed at the sensor, may cause the support medium to expand. A sensor of the invention may thus be light-addressable.

Other forms of interrogation are not remote, and include direct application of pressure, e.g. manually or by the application of a weight, in compression or stretching. The hologram may be sensitive to a physical effect such as temperature, whether increased or reduced.

The property of the support medium that varies may be its charge density, volume, shape, density, viscosity, strength, hardness, charge, hydrophobicity, swellability, integrity, cross-link density or any other physical property. Variation of such a property causes a variation of an optical characteristic, such as polarisability, reflectance, refractance or absorbance of the holographic element. If any change occurs whilst the hologram is being replayed by incident broad band, non-ionising electromagnetic radiation, then an optical property varies and a color or intensity change, for example, may be observed.

The property that varies is preferably the size or volume of the support medium. This may be achieved by incorporating into the support matrix, groups which cause an expansion or contraction of the support medium. The support medium preferably comprises a native or modified matrix with viscoelastic properties.

In a preferred embodiment, the support medium comprises a spiropyran group, or a derivative thereof. Spiropyrans, upon exposure to UV light, undergo a reversible conversion to merocyanine. This transformation is accompanied by an increase in charge, and may cause the support medium to expand. The conversion can be reversed by interrogating the sensor with visible light or heat.

In order to achieve a magnetic transition in the support medium, the medium may comprise a ferromagnetic polymer, or one or more "molecular magnets". Molecular magnets are known and can be synthesized as polymerisable monomers.

The holographic sensor may comprise a plurality of holographic elements, each element being sensitive to a different property. The holographic elements may be in the form of an array.

The hologram may be, for example, a transmission or reflection hologram. In a reflection hologram, the fringes are parallel to a surface of the support medium; this causes rays to leave by the same surface at which the incident rays enter. This fringe geometry provides a hologram that may be particularly sensitive to changes in temperature.

The sensitivity of the sensor to external physical interaction may be the consequence of the bulk properties of the sensor or support medium. Alternatively, it may be the consequence of chemical or other modification of the holographic element; this may be particularly appropriate for more sensitive reaction and/or to remote interrogation.

As illustrated in Example 2, a light-sensitive hologram can be fabricated by subjecting the sensor to interrogation by light, the properties of the hologram are altered in such a way that a change in an optical characteristic of the holographic element occurs. In Example 2, a particular bleach is used, but it will be understood that others are suitable. Modification of the bleaching protocol and/or the polymer backbone can be used to modulate photosensitivity. Similarly, other physical influences can be used to modulate sensitivity and thus the response of the sensor.

Alternative light-sensitive holographic sensors may be fabricated using an azobenzene moiety which undergoes a trans to cis photoisomerization under UV interrogation. This changes the free energy of mixing of the medium supporting the holographic image and therefore results in a change in the optical properties of the associated hologram. Yet another approach involves the use of triphenylmethane leuco dyes incorporated into the holograms. Such dyes photo-dissociate in the presence of UV light, resulting in a charged species which causes the holographic matrix to swell, altering the holographic image.

Particularly for a laser-sensitive sensor, the medium is preferably a polymer comprised of elastomeric monomers. Alternatively, the holographic medium may comprise a polymer such as poly(N-isopropylacrylamide) ("NiPAMM"), which has a conformation that is highly sensitive to changes in temperature. As the temperature rises, the rigid polymer structure collapses, producing a significant shift in the wavelength of reflection.

The invention is particularly relevant to security. For example, an authentication tag may comprise a holographic sensor having a built-in "message". When the sensor is interrogated, for example, say, with a magnetic field, the sensor displays the "message". The "message" is preferably viewable directly by eye.

Magnetic fields have the potential for use as security features. For example, simply by passing a magnet over a hologram, the resulting magnetic field would change the color or image of the hologram, showing that it was genuine. Furthermore, they could be used to create integrated magnetic strips (like those on credit cards) with holograms on them.

Pressure sensors could be used for food quality monitoring where a vacuum or a pressurized atmosphere is used to seal a product and keep it fresh. Loss of the vacuum or pressured atmosphere would change the hologram. Also, this could be an authenticity feature where pressure from touch changes the color or image to show that the hologram is genuine.

Other, temperature-sensitive embodiments of the invention are a device that changes color with the ambient temperature of, say, a fermentation system, or a replacement, power-free thermometer which can be interrogated from a distance using light. A security device which changes color when it comes close to body temperature, e.g. when pressing a finger onto it, or part of an array of sensors in bacterial or human diagnostics monitoring, are further embodiments.

The sensor may be sensitive to an analyte which is a chemical, biochemical or biological species. The present invention relates to a method of detection of any such analyte in a sample, which comprises contacting the sample with the sensor, and detecting any change of its optical characteristic.

The present invention also relates to an article comprising a sensor according to the invention where the article is a device such as a transaction card, banknote, passport, identification card, smart card, driving license, share certificate, bond, cheque, cheque card, tax banderole, gift voucher, postage stamp, rail or air ticket, telephone card, lottery card, event ticket, credit or debit card, business card, or an item used in consumer, brand or product protection for the purpose of distinguishing genuine products from counterfeit products or identifying stolen products. The article can also be an item of intelligent packaging which is a system that comprises a container, wrapper or enclosure to monitor, test or indicate product information on quality or environmental conditions that will affect product quality, shelf life or safety. Typical applications include indicators showing time-temperature, freshness, moisture, alcohol, gas, physical damage and the like.

The article can be an industrial or handicraft item comprising a decorative element, selected from items of jewellery, items of clothing (including footwear), fabric, furniture, toys, gifts, household items (including crockery and glassware), architecture (including glass, tile, paint, metals, bricks, ceramics, wood, plastics and other internal and external installations), art (including pictures, sculpture, pottery and light installations), stationery (including greetings cards, letterheads and promotional material) and sporting goods. The article can be a product or device for use in agricultural studies, environmental studies, human or veterinary prognostics, theranostics, diagnostics, therapy or chemical analysis which can be a test strip, chip, cartridge, swab, tube, pipette, contact lens, sub-conjunctival implant, sub-dermal implant, breathalyzer, catheter or a fluid sampling or analysis device.

The invention also relates to a transferable holographic film comprising a sensor according to the invention. The film can be present on a hot stamping tape or can be used to enhance the security of an article, by transferring onto the article the sensor from the film.

The present invention further relates to a product comprising a sensor of the invention which is capable of generating data and a system which uses such data for data reading, processing, storage, control, transmission, distributing, reporting and/or modeling. Such systems include mobile telephones, personal digital assistants and other portable electronic devices.

The following Examples illustrate the invention.

EXAMPLE 1

N-Isopropylacrylamide and N,N'-methylenebisacrylamide (MBA) in a molar ratio of 24:1 were dissolved in dimethyl sulphoxide (DMSO), to form a 40 wt % (of total monomer) solution. An appropriate amount of 5% 2,2-dimethoxy-2-phenylacetophenone (DMPA) in methanol was then added to the monomer solution to give a final concentration of 0.24% DMPA.

80 µl aliquots of the monomer solution were polymerized for 60 minutes using UV light under silanised glass slides. Holograms were recorded in these polymers using the silver diffusion method.

The hologram was incubated in 3.7 ml 20 mM sodium phosphate-buffered saline (pH 6.5, 30° C., ionic strength=50 mM) in a 4 ml cuvette. The temperature of the cuvette was modulated by an external water bath and temperature was measured in the bulk solution.

Figure 1:
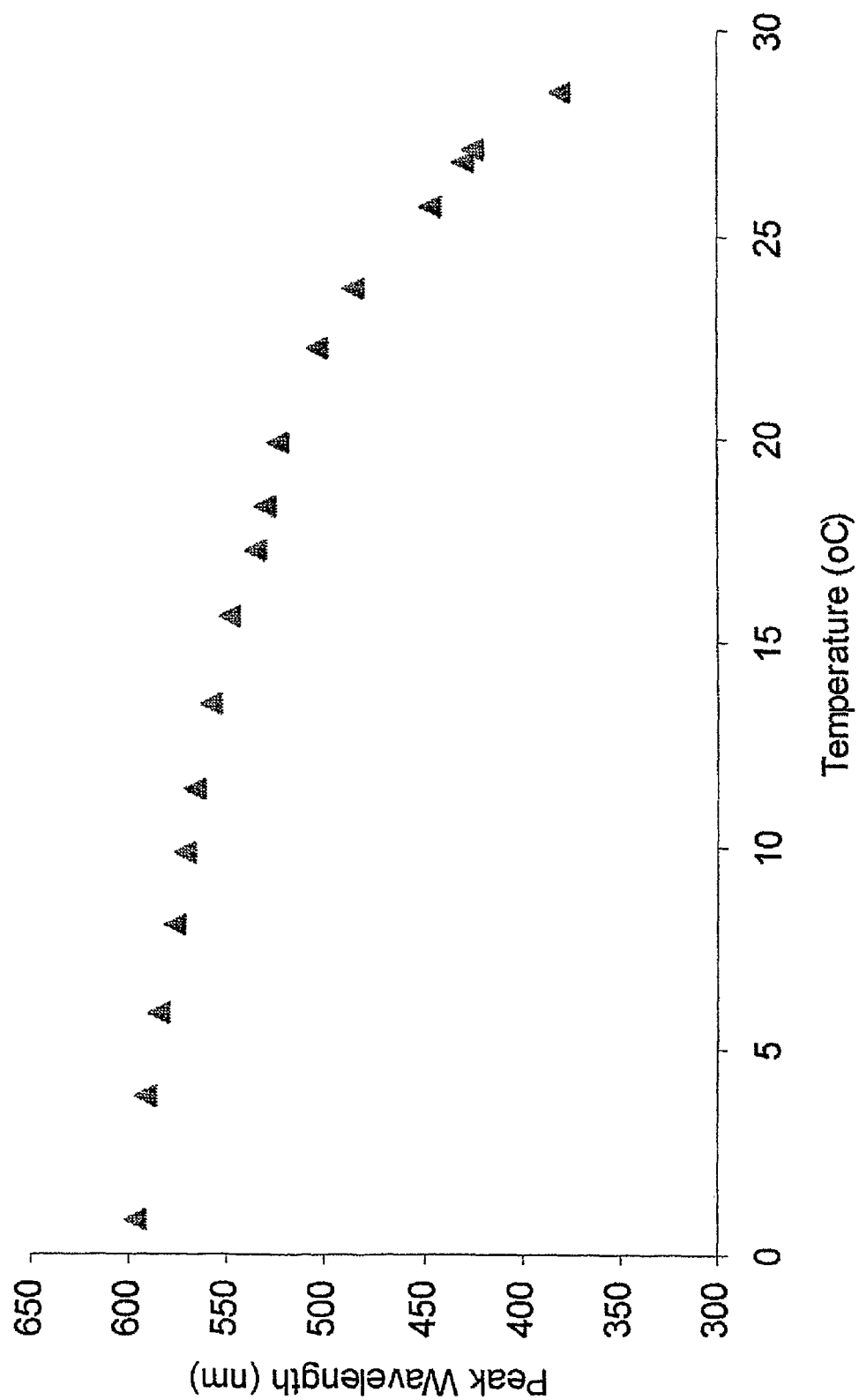
FIG. 1 is a graph of peak wavelength (nm) against temperature (°C.)

Peak diffraction wavelengths were recorded from spectral data acquired at an acute angle. All measurements reflect the final peak signals at equilibrium. Results are shown in FIG. 1 of the accompanying drawings.

EXAMPLE 2

Figure 2:
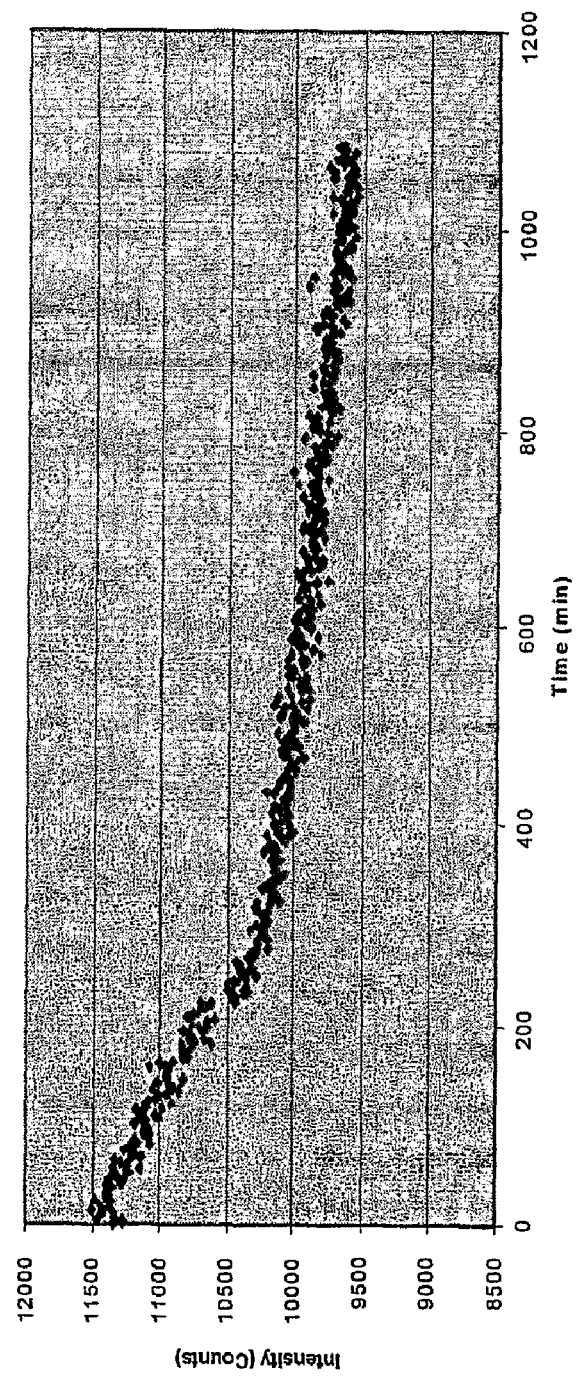
FIG. 2 is a graph of intensity (counts) against time (mins).

A light-sensitive holographic sensor was fabricated from a gelatin-based hologram. The resultant hologram was bleached using a Fe(III)-based formulation with KBr, to create photosensitive holographic fringes. The light-sensitive holographic sensor was then exposed to white light for 1000 min and the intensity of the light diffracted by the hologram was monitored and recorded for the duration of the experiment, as shown in FIG. 2 of the accompanying drawings. The intensity of the diffracted signal (reflectivity) was observed to decrease by 15% during the first 200 min of exposure to white light. Furthermore, this effect was visible to the naked eye.

EXAMPLE 3

An acrylamide co-polymer with a 2:1 ratio of acrylamide:methacrylamide and 5% of the cross-linker MBA was prepared. 200 µl of the monomer solution was polymerized onto a treated glass slide to create a thick polymer layer. A hologram was recorded within this polymer while it was soaking in a water bath using a frequency doubled Nd:YAG laser, resulting in a green diffraction signal (replay) of 529 nm in deionised water. The hologram was then covered with a second glass slide and clamped with a pair of G-clamps, spaced about 15 mm apart. The diffraction signal (replay) of the hologram in between the G-clamps changed to 526 nm once the clamps had been tightened, taking care not to crack the glass slides. The pressure of the clamps on the hologram resulted in a contraction in the volume of the hologram, thus causing the diffraction signal to blue-shift by a total of 3 nm.

EXAMPLE 4

A co-polymer of PANiCNQ, produced from polyaniline (PANi) and an acceptor molecule, tetracyanoquinodimethane (TCNQ) can be synthesized as described in WO03/062305 and in Zaidi et al, Polymer 45 (2004) 5683-89, the contents of which are incorporated herein by reference. This gives rise to a polymer material that exhibits magnetic properties at room temperature. The polymer can be coated onto a glass surface and used as is or cross-linked by diffusion of co-monomers containing cross-linkers into the PANiCNQ and polymerizing them. The PANiCNQ polymer can then be treated as a recording material using silver diffusion, as described in WO95/26499, to produce a hologram. Alternatively, the monomer solution can be cross-linked using a UV laser, to produce silver-free holograms, as described in WO2004/081676.

As the entire polymer is magnetic, on interrogation with a magnetic field, the polymer can be made to expand or contract, thereby red-shifting or blue shifting respectively, the diffraction wavelength (replay) of the hologram when it is illuminated with white light. This could be used to quantify the magnetic field or to cause a change in the color/image of the hologram in the presence of a suitable magnetic field.

The invention claimed is:

1. A sensing method, which comprises:
    subjecting a holographic sensor to an external physical interaction, wherein the sensor is a volume hologram recorded in a support medium that is directly sensitive to the external physical interaction, wherein the volume hologram produces a holographic image; and
    observing a change in the holographic image;
    wherein the external physical interaction is temperature, and wherein the change in the holographic image is a change of color or a change of image to show that the volume hologram is genuine;
    wherein the support medium is a polymer that is highly sensitive to changes in temperature such that the polymer has a rigid structure which collapses upon an increase in temperature, thereby producing a significant shift in a wavelength of reflection of the polymer; and
    wherein the volume hologram comprises a reflection hologram.

2. The method according to claim 1, wherein the support medium comprises a polymer.

3. The method according to claim 1, wherein the change in the holographic image is reversible.

4. The method according to claim 3, wherein the change in the holographic image is a change of color or a change of image to show that the volume hologram is genuine for the purpose of authentication.

5. The method according to claim 1, wherein the volume hologram is viewable under white light, UV light or infra-red radiation.

6. The method according to claim 1, wherein the change in the holographic image is a change of color or a change of image to show that the volume hologram is genuine for the purpose of authentication.

7. The method according to claim 1, wherein the polymer is poly(N-isopropylacrylamide).

8. A sensing method, which comprises:
    subjecting a holographic sensor to an external physical interaction, wherein the sensor is a volume hologram recorded in a support medium that is directly sensitive to the external physical interaction, wherein the volume hologram produces a holographic image; and
    observing a change in the holographic image;
    wherein the external physical interaction is magnetism, and wherein the change in the holographic image is a change of color or a change of image to show that the volume hologram is genuine;
    wherein the support medium is magnetic; and
    wherein the volume hologram comprises a reflection hologram.

9. The method according to claim 8, wherein the support medium comprises a polymer.

10. The method according to claim 8, wherein the change in the holographic image is reversible.

11. The method according to claim 8, wherein the volume hologram is viewable under white light, UV light or infra-red radiation.

12. The method according to claim 8, wherein the change in the holographic image is a change of color or a change of image to show that the volume hologram is genuine for the purpose of authentication.

13. The method according to claim 10, wherein the change in the holographic image is a change of color or a change of image to show that the volume hologram is genuine for the purpose of authentication.

14. The method according to claim 8, wherein the support medium comprises a molecular magnet.

15. The method according to claim 8, wherein the support medium comprises a ferro-magnetic polymer.

16. The method according to claim 8, wherein the support medium comprises a ferri-magnetic polymer.

17. The method according to claim 8, wherein the support medium is a copolymer of aniline and tetracyanoquinoline.

* * * * *